United States Patent
Philp, Jr. et al.

(10) Patent No.: US 8,308,479 B2
(45) Date of Patent: Nov. 13, 2012

(54) METHOD AND APPARATUS FOR TOOTH WHITENING

(75) Inventors: Graham K. Philp, Jr., Naples, FL (US); Damon J. Brown, Boston, MA (US); Tim Diasti, Clearwater, FL (US)

(73) Assignee: Dentovations Inc., Boston, MA (US)

(*) Notice: Subject to any disclaimer, the term of this patent is extended or adjusted under 35 U.S.C. 154(b) by 0 days.

(21) Appl. No.: 12/379,051

(22) Filed: Feb. 11, 2009

(65) Prior Publication Data

US 2009/0148815 A1 Jun. 11, 2009

Related U.S. Application Data (63) Continuation of application No. 11/293,497, filed on Dec. 5, 2005, now abandoned, which is a continuation of application No. PCT/US2004/010953, filed on Apr. 20, 2004.

(60) Provisional application No. 60/524,861, filed on Nov. 26, 2003.

(51) Int. Cl.
*A61C 3/00* (2006.01)
*A61C 5/00* (2006.01)

(52) U.S. Cl. .............................. 433/29; 433/32; 433/215

(58) Field of Classification Search .................. 433/29, 433/32, 215
See application file for complete search history.

(56) References Cited

U.S. PATENT DOCUMENTS

| | | | |
|---|---|---|---|
| 3,278,520 A | 10/1966 | Klug | |
| 3,278,521 A | 10/1966 | Klug | |
| 3,567,823 A | 3/1971 | Yamaga et al. | |
| 4,450,139 A | 5/1984 | Bussiere et al. | |
| 4,556,561 A | 12/1985 | Brown et al. | |
| 4,661,070 A * | 4/1987 | Friedman | 433/203.1 |
| 4,684,517 A | 8/1987 | Clipper et al. | |
| 4,952,143 A | 8/1990 | Becker et al. | |
| 4,976,955 A | 12/1990 | Libin | |
| 4,980,152 A | 12/1990 | Frazier et al. | |
| 4,983,380 A | 1/1991 | Yarborough | |

(Continued)

FOREIGN PATENT DOCUMENTS

EP 0539315 A2 4/1993

(Continued)

OTHER PUBLICATIONS

Goldstein et al., eds., Complete Dental Bleaching, Ch. 4, Quintessence Publishing Co., Inc., Chicago (1995).

(Continued)

*Primary Examiner* — Heidi M Eide
(74) *Attorney, Agent, or Firm* — Shlesinger, Arkwright & Garvey LLP (57) ABSTRACT

Preconditioning mouth rinse, which pre-treats the teeth to better receive a whitening formula containing a photosensitive compound, and a hand-held consumer light source for tooth whitening, which provides rapid tooth whitening, are disclosed. The light source may use a specific range of visible light and also emit heat sufficient to raise the temperature of the teeth a desired amount at a depth up to about 2 mm in the range of about from 1-5° Celsius over a predetermined period of time. The specified wavelengths of the hand-held consumer operable light will activate the photosensitive substance in the whitening formula. The oxidizing compounds may be transparent to light enabling light energy to activate the oxidizing compounds directly on the tooth surface, or to activate a photosensitizing or photosensitive compound added to produce the desired temperature increase.

11 Claims, 3 Drawing Sheets

U.S. PATENT DOCUMENTS

| | | | |
|---|---|---|---|
| 4,983,381 | A | 1/1991 | Torres Zaragoza |
| 5,000,942 | A | 3/1991 | Libin |
| 5,009,885 | A | 4/1991 | Yarborough |
| 5,032,178 | A | 7/1991 | Cornell |
| 5,084,268 | A | 1/1992 | Thaler |
| 5,098,303 | A | 3/1992 | Fischer |
| 5,139,768 | A | 8/1992 | Friedman |
| 5,171,564 | A | 12/1992 | Nathoo et al. |
| RE34,196 | E | 3/1993 | Munro |
| 5,208,010 | A | 5/1993 | Thaler |
| 5,217,710 | A | 6/1993 | William et al. |
| 5,234,342 | A | 8/1993 | Fischer |
| 5,264,205 | A | 11/1993 | Kelly |
| 5,279,816 | A | 1/1994 | Church et al. |
| 5,290,566 | A | 3/1994 | Schow et al. |
| 5,302,375 | A | 4/1994 | Viscio |
| 5,310,563 | A | 5/1994 | Curtis et al. |
| 5,372,802 | A | 12/1994 | Barrows et al. |
| 5,376,006 | A | 12/1994 | Fischer |
| 5,395,241 | A | 3/1995 | Kandelman |
| 5,403,577 | A | 4/1995 | Friedman |
| 5,403,578 | A | 4/1995 | Gordon |
| 5,409,631 | A | 4/1995 | Fischer |
| 5,425,953 | A | 6/1995 | Sintov et al. |
| 5,437,858 | A | 8/1995 | Hungerbrach et al. |
| 5,457,611 | A | 10/1995 | Verderber |
| 5,614,174 | A | 3/1997 | Hsu et al. |
| 5,631,000 | A | 5/1997 | Pellico et al. |
| 5,645,428 | A | 7/1997 | Yarborough |
| 5,690,912 | A | 11/1997 | Campbell et al. |
| 5,693,315 | A | 12/1997 | Bevilacqua |
| 5,698,182 | A | 12/1997 | Prencipe et al. |
| 5,708,052 | A | 1/1998 | Fischer et al. |
| 5,713,738 | A | 2/1998 | Yarborough |
| 5,718,886 | A | 2/1998 | Pellico |
| 5,746,598 | A | 5/1998 | Fischer |
| 5,766,574 | A | 6/1998 | Christina-Beck et al. |
| 5,780,015 | A | 7/1998 | Fisher et al. |
| 5,785,527 | A | 7/1998 | Jensen et al. |
| 5,785,957 | A | 7/1998 | Losee et al. |
| 5,792,446 | A | 8/1998 | Ashley |
| 5,797,749 | A | 8/1998 | Bertolotti et al. |
| 5,814,304 | A | 9/1998 | Wong et al. |
| 5,820,852 | A | 10/1998 | Burgess et al. |
| 5,824,289 | A | 10/1998 | Stoltz |
| 5,846,570 | A | 12/1998 | Barrow et al. |
| 5,849,266 | A | 12/1998 | Friedman |
| 5,849,269 | A | 12/1998 | Burgess et al. |
| 5,851,512 | A | 12/1998 | Fischer |
| 5,855,870 | A | 1/1999 | Fischer |
| 5,858,332 | A | 1/1999 | Jensen et al. |
| 5,879,691 | A | 3/1999 | Sagel et al. |
| 5,891,453 | A | 4/1999 | Sagel et al. |
| 5,902,568 | A | 5/1999 | Ryles et al. |
| 5,922,307 | A | 7/1999 | Montgomery |
| 5,928,628 | A | 7/1999 | Pellico |
| 5,985,249 | A | 11/1999 | Fischer |
| 6,030,222 | A | 2/2000 | Tarver |
| 6,036,493 | A | 3/2000 | Sharma |
| 6,102,696 | A | 8/2000 | Osterwalder et al. |
| 6,149,895 | A | 11/2000 | Kutsch |
| 6,162,055 | A | 12/2000 | Montgomery et al. |
| 6,183,251 | B1 | 2/2001 | Fischer |
| 6,254,388 | B1 | 7/2001 | Yarborough |
| 6,312,666 | B1 | 11/2001 | Oxman et al. |
| 6,331,111 | B1 | 12/2001 | Cao |
| 6,331,292 | B1 | 12/2001 | Montgomery |
| 6,343,933 | B1 | 2/2002 | Montgomery |
| 6,391,283 | B1 * | 5/2002 | Jensen et al. ................ 424/49 |
| 6,416,319 | B1 | 7/2002 | Cipolla et al. |
| 6,419,906 | B1 | 7/2002 | Xu et al. |
| 6,514,543 | B2 | 2/2003 | Montgomery |
| 6,517,350 | B2 | 2/2003 | Diasti et al. |
| 6,536,628 | B2 | 3/2003 | Montgomery |
| 2001/0046652 | A1 * | 11/2001 | Ostler et al. ................ 433/29 |
| 2002/0004190 | A1 | 1/2002 | Diasti et al. |
| 2002/0047222 | A1 | 4/2002 | Philp |
| 2002/0064753 | A1 | 5/2002 | Philp |
| 2002/0177099 | A1 | 11/2002 | Cao |
| 2003/0017435 | A1 | 1/2003 | Ibsen et al. |
| 2003/0036037 | A1 | 2/2003 | Zavitsanos et al. |
| 2003/0091954 | A1 | 5/2003 | West et al. |
| 2005/0255054 | A1 | 11/2005 | Philp et al. |
| 2005/0260142 | A1 | 11/2005 | Philp et al. |
| 2006/0141422 | A1 | 6/2006 | Philp et al. |
| 2006/0141423 | A1 | 6/2006 | Brown et al. |
| 2007/0009857 | A1 | 1/2007 | Philp et al. |
| 2009/0148815 | A1 | 6/2009 | Philp et al. |
| 2009/0325129 | A1 | 12/2009 | Brown et al. |

FOREIGN PATENT DOCUMENTS

| | | |
|---|---|---|
| WO | 98/58595 | 12/1998 |
| WO | WO 9940870 A1 | 2/1999 |
| WO | WO 0126576 A1 | 10/2000 |
| WO | WO 00/67048 | 11/2000 |

OTHER PUBLICATIONS

The Dental Advisor Plus, vol. No. 1, (Jan./Feb. 1996).
C. G. Toh, "Clinical Evaluation of a dual-activated bleaching system"; Asian J. Aesthet. Dent, I: 65-70, (1993).
Union Broach Operator's Manual, "Operating Instructions Illuminator," Union Broach, A Health-Chem Company, pp. 1-15, cited in U.S. 6,162,055 before Dec. 2000.
QuasarBrite™, Contrast A.M.®, Laser Whitening Gel, Instructions for Use Manual, Interdent, Inc. (Los Angeles, CA), cited in U.S. 6,162,055 before Dec. 2000.
Shofu®, HiLite® Dual Activated Bleaching System, Instruction Manual, Shofu Dental Corporation (Menlo Park, CA), Nov. 1997.
European Patent Office Communication dated Mar. 31, 2009, including the Supplementary Partial European Search Report dated Mar. 17, 2009. (4 pages).

* cited by examiner

METHOD AND APPARATUS FOR TOOTH WHITENING

CROSS-REFERENCE TO RELATED APPLICATIONS

This application is a continuation of U.S. application Ser. No. 11/293,497, filed Dec. 5, 2005 now abandoned, which application Ser. No. 11/293,497 is a continuation of Application No. PCT/US2004/010953 to Philp, Jr. et al., filed 20 Apr. 2004, which claims the priority of Application No. PCT/US2003/017631 to Brown, Jr. et al., filed 5 Jun. 2003, and this application claims the priority of U.S. patent application No. 60/524,861 to Philp, Jr. et al., filed 26 Nov. 2003, and each of which is incorporated herein by reference.

This application relates to applicant's concurrently filed application Ser. No. 11/293,499, entitled "Method for Whitening Teeth", filed Dec. 5, 2005, and which is incorporated herein by reference.

FIELD OF INVENTION

The invention relates to a method and apparatus for achieving rapid tooth whitening, which is usable by a consumer. In particular, the invention relates to a preconditioning mouth rinse, which prepares teeth to receive the whitening formula, a whitening compound, which is directly applied onto teeth and which contains a photoactive substance, which responds to a safe wavelength of visible light. Also included in the invention is a hand held consumer light, which emits a biologically safe wavelength of light to assist in the whitening of teeth, such as by activating the tooth-whitening photoactive substance.

BACKGROUND OF THE INVENTION

Teeth become discolored with age, blood, amalgam restorations, antibiotics such as tetracycline, and substances in food, beverages, tobacco and salivary fluid. Tooth structures which are responsible for a stained appearance are enamel, dentin, and the acquired pellicle.

Tooth enamel is predominately formed from an inorganic substance, hydroxyapatite crystals, along with approximately 5% organic materials, predominantly collagen. The dentin is composed of about 20% protein including collagen; the balance of inorganic materials including hydroxyapatite crystals. The acquired pellicle is a proteinaceous layer on the surface of tooth enamel, and that may be removed after an intensive tooth cleaning.

Tooth stains are generally classified as either extrinsic or intrinsic, depending on whether the stain is on the surface of the tooth within the acquired pellicle or within the tooth structure itself within the enamel or dentin. For example, extrinsic staining of the acquired pellicle can occur from foods or compounds, which contain tannins and other polyphenolic compounds which become trapped in the lightly bound proteinaceous layer on the surfaces of the teeth.

Intrinsic staining, on the other hand, occurs when chromogens and pre-chromogens penetrate the enamel and dentin and become tightly bound to the tooth structure. Intrinsic staining can occur when blood or amalgam products leach into the enamel and dentin. Intrinsic staining likewise can occur systemically from excess fluoride intake during enamel development leading to a mottled yellow or brown stain of fluoresce staining. Intrinsic staining is not removable by mechanical methods of tooth cleaning and generally requires the use of chemicals, for example strong oxidizing agents such as hydrogen peroxide which can penetrate into the tooth structure to effect a change in the light absorbtivity of the stain chromogen and/or the solubility of the chromogens.

The desire for whiter, lighter teeth is considered to be cosmetic and desirable in today's cosmetically-orientated society. Tooth bleaching is generally accomplished by gels, pastes, or liquids which contain an oxidizing agent such as hydrogen peroxide that attack (i.e., chemically react with) the chromogen molecules, making them colorless and/or water soluble, making the tooth appear lighter and brighter, thus resulting in lighter brighter teeth.

The most commonly used oxidizing agent is hydrogen peroxide ($H_2O_2$), such as from carbamide peroxide, which is mixed with an anhydrous viscous carrier containing glycerin and/or propylene glycol and/or polyethylene glycol. When in contact with water, carbamide peroxide dissociates into urea and hydrogen peroxide. The hydrogen peroxide in the presence of water then disassociates into water and a nascent oxygen anion species. It is these highly-nascent oxygen species, which react with the stain making them more water soluble, transparent, or both.

There are several known delivery systems to deliver carbamide peroxide to the surfaces of the teeth.

A common approach is to have a dental professional construct a custom-made tray from an impression of the patient's teeth. The oxidizing gel is dispensed into the tray by the patient and the tray is worn over the teeth intermittently for a period of two weeks to several months, depending on the severity of the staining. This approach can cause tooth sensitivity in over 50% of the patients, and it can be uncomfortable for the patients to wear the tooth bleaching trays. Tooth sensitivity is believed to result from the movement of fluid through the dentinal tubules, which is sensed by nerve endings within the tooth. The carriers, glycerin propylene glycol and polyethylene glycol, draw fluids toward them and therefore contribute to the tooth sensitivity often experienced by wearing a bleaching tray.

Another approach is to incorporate the oxidizing agent in a strip and have the patient wear the strip intermittently over a period of two weeks. This approach also has the disadvantage of being awkward for patients to wear, and many patients wearing the strips, also experience tooth sensitivity. Further, the strips have an inherent problem of contacting the teeth only on the facial surfaces and most of the staining occurs in between the teeth in the interproximal areas where in can be difficult to place the strip, having it in contact with the tooth.

Another recent approach is to simply paint on the oxidizing agent, carbamide peroxide or hydrogen peroxide, directly on the teeth. In products, which are gels containing glycerin and/or propylene glycol or polyethylene glycol, tooth sensitivity can be experienced, and the gels can easily be removed by the lips and tongue, thereby decreasing their effectiveness.

One approach involves dissolving carbamide peroxide in alcohol, and a resin. The resultant compound is applied directly onto the teeth, and the alcohol evaporates, leaving a sticky resin film or precipitate remaining on the surface, of the teeth. When saliva contacts the teeth, the peroxide is released in a relatively strong concentration for a period of up to 20 minutes. This product contains no glycerin, propylene glycol, or polyethylene glycol and tooth sensitivity is lessened with some resultant whitening. These products take approximately two weeks of use several times a day to achieve a desired result.

To address the problem of taking excessive time to whiten teeth, manufacturers developed systems used by a dentist and only available in a dental office (with and without a light source), to whiten teeth in approximately one hour. These systems generally use oxidizing compositions (hydrogen peroxide up to 35%), which are applied directly on the surfaces of the teeth in a dental office under the supervision of a dentist or dental hygienist. Owing to the high concentration of oxidizing agents contained in these in-office products, they can be hazardous to the patient if not handled carefully. The patient's soft tissues—gingiva, lips and tissues—must be isolated from potential exposure to a concentration of oxidizing agent by the use of a rubber dam or by covering the soft tissues with a polymerizable resin that is shaped to conform to the gingival contours and subsequently cured by a high intensity light source operable only by a dentist. These dentist in-office whitening systems are expensive to the patient.

Known patents directed to these various tooth whitening systems include:

U.S. Pat. No. 4,952,143 to Becker et al.; and
U.S. Pat. No. 5,032,178 to Cornell.

These known systems have drawbacks.

A commercial product, called Opalescence, from Attica Dental Products, Inc., South Jordan, Utah is known.

Further known systems are set forth in:

U.S. Pat. No. 5,785,527 to Jensen et al.; and
U.S. Pat. No. 6,517,350 to Diasti et al.

One commercially available illuminating system is from Union Broach, a Health/Claim Company, New York, N.Y.

Other known United States patent documents include:

U.S. Pat. No. 4,450,139 Bussiere et al.;
U.S. Pat. No. 5,457,611 Verderber;
U.S. Pat. No. 6,331,111 Cao;
U.S. Pat. No. 6,343,933 Montgomery;
U.S. Pat. No. 6,416,319 Cipolla;
U.S. Pub. No. 2003/0017435 Ibsen et al.;
U.S. Pub. No. 2003/0036037 Zavitsanos et al.; and
U.S. Pat. No. 4,661,070 to Friedman.

There is a need for improved compositions and devices for whitening teeth that are capable of whitening the teeth rapidly and inexpensively by consumers without damaging the tooth enamel, dentin, or the pulp, and that are able to be used at a lower concentration of peroxide, thus enabling the patient to use the product at home without harming the tissues, or causing tissue irritation, or causing tooth sensitivity.

OBJECTS AND SUMMARY OF THE INVENTION

It is an object of the invention to provide a tooth whitening method, system, and device that overcome the drawbacks of prior art methods, systems, and devices.

It is a further object of the invention to provide a tooth whitening system, which provides a more even whitening of the teeth than known systems.

It is yet another object of the invention to provide a tooth whitening system, which is self-regulating and avoids overheating of the user's teeth being whitened, for example.

Another object of the invention is to provide a tooth whitening system, which may be performed without the use of a dental dam or without protecting the oral tissues by covering them with a polymerizable resin.

It is an object of this invention to provide a tooth whitening system, the action of which is accelerated by light-and-heat energy, which the consumer can use at home, thereby being more cost-effective than in-office teeth whitening regimes.

It is a further object of this invention to provide a tooth whitening system, which shortens the treatment time to obtain a given level of whitening using at-home paint-on whitening products or bleaching tray regimes.

Another object of this invention is to use a solution or gel which temporarily adheres to the teeth, and which can be directly applied to the teeth by consumers at their home or elsewhere.

It is yet another object of this invention to use a solution or gel with a concentration of peroxide which will reduce or eliminate irritation of the patient's tissues making it better and more comfortable for the patient.

A further object of the invention is to provide a preconditioning mouth rinse formulated to prepare teeth for a tooth whitening agent.

It is yet another object of this invention to use a hand-held light source which uses batteries or a rechargeable power source, and that can provide an even illumination of visible- and light-heat in the range of 1° to 5° C. against the surfaces of the front anterior teeth.

It is a further object of this invention that the light/heat source of light be controlled so as not to exceed a 5° C. increase in temperature no matter how long the consumer applies the light/heat source to the surfaces of the anterior teeth.

It is a further object of this invention to use a liquid solution or gel which is relatively transparent and allows the transmission of heat into the enamel or dentin to achieve a temperature increase of about 1° to 5° C. for approximately 1-2 minutes to effect a biologically-compatible and effective level of tooth whitening.

Another object is to provide a tooth whitening device including a hand-held light source used by the consumer that produces a slight increase in temperature of from 1°-5° C. either on the surface of the tooth directly or within the tooth structure at a depth of 1-2 mm from the surface with the use of photosensitive compounds for producing the slight increase in temperature.

A further object is to provide a tooth whitening device with an attachment which is curved to simulate the natural curvature of the arch of the teeth, and which is provided in several sizes; e.g., small, medium, and large.

A further object is to provide a tooth whitening device with a timer which automatically turns the light source off at the desired time along with a device for indicating the light source is on.

DETAILED DESCRIPTION OF THE INVENTION

These embodiments are set forth to describe and illustrate the invention, but are not intended to be limiting. The invention may achieve rapid tooth whitening by using a preconditioning rinse and hand held consumer light for emitting optical energy and a safe amount of heat to penetrate an oxidizing compound placed directly on the tooth surface to be whitened.

There are known compositions that include light (or heat), which can be added to an oxidizing compound (e.g. gel or solution) and dispersed directly in and homogenously throughout the oxidizing compound. Some references and text are noted: for example Kirk-Othmer Encyclopedia of Chemical Technology, 4th edition, volumes 4 (1992), 13 (1995), 18 (1996), John Wiley & Sons, N.Y.; Goldstein and Garber, Complete Dental Bleaching, Quintessence Publishing Co. 1995; and the Journal of the American Dental Association, Vol. 128, Special Supplement, April 1997.

For tooth whitening the greatest oxidizing activity is required in the first few millimeters of enamel and in the dentin at the tooth surface.

The present invention is more effective at removing teeth stains at lower levels of active oxidizing agents and lower levels of heat than known devices, thereby resulting in a better whitening system which can be used safely by a consumer and which can result in more rapid tooth whitening. To better understand the tooth whitening process in the present invention some background information is desirable.

The oxidizing agent, in the present invention, may be carbamide peroxide (urea hydrogen peroxide). This agent is broken down in the presence of water to urea and hydrogen peroxide ($H_2O_2$). The hydrogen peroxide is unstable and in the presence of light or moisture it decomposes into water $H_2O$ and an Oxygen free radical (i.e., $O^-$ or nascent oxygen species or oxygen free radicals). It is these oxygen free radicals, which attack the stain molecules and make them water-soluble, transparent, or both, resulting in the lighter brighter teeth.

The oxygen free radicals which are formed are highly reactive and will react with each other to produce $O_2$ (Oxygen) rapidly. It is the ability and quantity of the free radical oxygen anions to reach the stain molecules and react with them, which determines the efficacy of the whitening process. The speed of the whitening process can be significantly enhanced with the addition of a slight amount of heat in that solution (dissolving) occurs more rapidly in a warmer environment than a cooler one, for example.

Detailed Description of the Mouth Rinse

The invention achieves rapid tooth whitening by using a preconditioning mouth rinse, which prepares the tooth surface to receive the whitening compound alone with a photosensitive compound in the whitening compound followed by using optical energy which penetrates through the existing formulation, which is placed on the tooth surface to be whitened.

To enhance tooth whitening at the surface of and within the first few millimeters of enamel below the surface, the present invention includes a preconditioner, such as a preconditioning mouth rinse, which prepares the teeth to receive the whitening compound. The mouth rinse is formulated to kill bacteria which produce peroxidase enzymes, create an environment on the tooth surface which has a slightly basic pH, and contains a surfactant thereby improving wetting of the tooth surface by the whitening compound and allowing deeper penetration. The surfactant will also help the oxygen free radicals react with the tooth stain (chromogen molecules) and within the tooth surface; the mouth rinse may also contain substances which destroy and prevent oral malodors and flavoring compounds.

The mouth contains peroxide enzymes including salivary peroxidase, catalases and bacteria, which produce peroxidases, which are enzymes which destroy peroxide. It would be desirable to have in the preconditioning or activator mouth rinse a disinfectant which would kill the bacteria which produce peroxidases thereby increasing the quantity of hydrogen peroxide, which produces the oxygen free radicals.

Common disinfectants in known mouthwash preparations may be used.

If the pH in the environment of the oxidizing compound, hydrogen peroxide, for example, is increased, the oxidizing compound will degrade and generate free radicals more readily. Furthermore, most peroxidase enzymes (including salivary peroxides and catalases) have low activities above a pH of 8.

It is therefore desirable to have an alkaline pH in the activator rinse to pre-treat the environment agent to have a pH of about 8. Sodium bicarbonate, which is safe and commonly used in dental toothpastes and rinses, has a pH of 8.2. The ideal pH to break down hydrogen peroxide is between a pH range of 7.9-9.0, a higher pH can become caustic to the oral tissues.

pH Adjusting Chemicals

Sodium carbonate, potassium carbonate, sodium hydroxide, ammonium hydroxide, potassium hydroxide, sodium phosphate di- and tri-basic, potassium phosphate di- and tri-basic, sodium tripolyphosphate, tris(hydroxymethyl)aminomethane, polyethylenaimine, triethanolamine, and other alkaline agents. Acidic pH adjusting agents, such as citric acid, phosphoric acid, and others may also be used alone or in conjunction with an alkaline pH adjusting agent to obtain the desired pH and to provide buffering capacity.

The performance enhancing adjuvant may include at least one of a buffer, a surfactant, a thickener, a film forming ingredient, a penetration enhancer, and desensitizing agent.

Surfactants (Surface Active Agents)

Surfactants may be used to lower the surface tension of the compositions. Lowering of the surface tension allows for better wetting and spreading of the composition on the tooth surface. Some surfactants, such as zwitterionic and fluorinated surfactants, have been seen to increase the penetration of the present inventive compositions into the tooth structure.

Useful surfactants may include those identified in U.S. Pat. No. 5,279,816 to Church et al. and U.S. Pat. No. 5,302,375 to Viscio, each of which is incorporated herein by reference in its entirety.

Zwitterionic surfactants have positive and negative charges that significantly improve penetration of peroxide into the tooth. It is to be understood that additional useful surfactants will become apparent to those skilled in the art based upon the disclosure herein. The level of surfactant, when present, may be from about 0.001% to about 10.0% by weight of the accelerator composition, and may be from about 0.1% to about 1% by weight of the accelerator composition.

Thickeners

A thickener may also be added to the accelerator composition as a performance enhancing adjuvant to increase the contact time of the accelerator on the tooth surface.

In one embodiment, the thickener provides coating properties for the accelerator by forming a film when applied to the teeth.

Thickeners such as neutralized carboxypolymethylene and other polyacrylic acid polymers and copolymers, hydroxypropylcellulose and other cellulose ethers, salts of poly(methyl vinyl ether-co-maleic anhydride), polyvinyl pyrrolidone (PVP), poly(vinylpyrrolidone-co-vinyl acetate), silicon dioxide, fumed silica, stearic acid esters, and others are found to have utility in the formulation of the oxidizing compositions and tooth whitening accelerator compositions.

Polymers utilized as thickeners may also serve as film-forming agents that provide for even distribution of the accelerator composition over the tooth surface. It is to be understood that additional useful thickeners will become apparent to those skilled in the art based upon the disclosure herein.

The level of thickener, when present, is highly dependent upon the type chosen, but in general may be included in the composition at a concentration of from about 0.1% to about 20.0% by weight of the composition, and may be at a concentration of from about 0.1% to about 5% by weight of the accelerator composition.

Flavorants

Flavorants may also be included in the accelerator composition in order to improve palatability and acceptance by the user or the patient. Flavorants are generally known in the art and include, among others, spearmint, peppermint, anethole, menthol, stevia, citrus flavors, and vanilla.

It may be desirable to provide within the composition an artificial sweetener selected from the group including sodium saccharin and potassium acesulfame. Sugars and sugar alcohols, such as sucrose, fructose, glucose, xylitol, maltitol, mannitol, sorbitol, and other mono-, di-, tri-, and higher monosaccharides may be used as sweeteners. For example, glycine may also serve as a sweetener and has the ability to mellow saltiness and bitterness of the pH adjusting agent. Both flavorants and sweeteners, when present, may each be included at a level of from about 0.01% to about 5.0% by weight of the composition.

Other artificial sweeteners are contemplated to have utility in the practice of the present invention, limited only by their solubility and stability in the compositions.

Example of Formula for Mouth Rinse

| Ingredient | Concentration | Supplier and miscellaneous information |
| --- | --- | --- |
| NP-9, ethoxylated nonylphenol, 9 molar EO. | 0.65 mls | Brenntag, Univar |
| Peppermint Oil | 1.4 mls | Lebermuth |
| Nutrasweet ® Granular 100 | 0.75 grams | The Nutrasweet Company |
| Glycerin 99.5% Kosher food grade | 30 mls | Brenntag, Univar |
| Sodium Bicarbonate food grade | 2 grams | Brenntag, Univar |
| Sodium Carbonate food grade | 0.1 grams | Brenntag, Univar |
| Benzethonium Chloride | 0.15 grams | Lonza Inc |
| Purified Water | Balance to 1 gallon (i.e., 3.785 liter) | Distilled or deionized or reverse osmosis grade |
| Ethanol 75% or greater | ~10 mls | Food Grade |

Detailed Description of the Directly Applied Tooth Whitening Formula

Along with a safe concentration of an oxidizing agent of approximately 8-12% carbamide peroxide by weight the oxidizing solution or gel can be incorporated with light-activated photosensitizing agents, which can include any compounds capable of absorbing light energy at biologically acceptable wavelengths for use in the oral cavity.

Examples of compounds which may convert light energy to heat or chemical energy include readily available compounds, such as semiconductor particles, e.g., titanium oxide and/or zinc oxide. If photosensitizers are used, such may be allowed to penetrate into the enamel or dentin prior to the application of the light, depending on the intended use and the chemical composition of the whitener used. Therefore the particle size should enable penetration of the photoactive substance.

Example of Tooth Whitening Formula

| COMPOUND | % by Weight | RANGE % |
| --- | --- | --- |
| Ethyl Alcohol | 73.75 | |
| Hydrogenated Ester of Rosin | 13.87 | 0.001-35.00 |
| Urea (Carbamide) Hydrogen Peroxide | 11.10 | 0.001-25.00 |
| Hydroxypropylcellulose 1500 cps | 0.55 | 0.001-10.00 |
| Flavoring - Menthol | 0.22 | 0.001-15.00 |
| Flavoring - Peppermint Oil | 0.20 | 0.001-15.00 |
| Zinc Oxide (micro particles) | 0.15 | 0.001-5.00 |
| Flavoring - Aspartame | 0.15 | 0.001-5.00 |

A supplier of the zinc oxide (micro particles) is B.F. Goodrich.

Example of Alternative Formula

| COMPOUND | %/w | RANGE |
| --- | --- | --- |
| Anhydrous Propylene Glycol | 54.3% | 0.001-75.00 |
| Fumed Silica | 20% | 0.001-40.00 |
| Sodium Perborate Monohydrate | 25% | 0.001-40.00 |
| Sodium Saccharine | 0.7% | 0.001-5.00 |

Viscous whitening agent which may be painted on the teeth may be as follows.

The viscosity of one or more of whitening agents may be varied depending on the intended use, as described in detail below.

The whitening agent may be a "paint-on" whitening agent which can be applied to the teeth, adheres to the teeth, and requires no protective tape, film, or cover when on the teeth to avoid being wiped off by the user's gums or saliva. Please see Applicant's co-pending application no. PCT/US03/17631, filed 5 Jun. 2003, and which is incorporated herein by reference.

It is contemplated that in any of the embodiments of any suitable viscous, solid or semi-solid whitening agent may be used that can whiten without irritating the mouth tissues.

In an embodiment of the invention, the whitening agent may have the following range of compositions.

| WHITENING AGENT COMPOSITION A2 (to yield 100 ml of composition) | |
| --- | --- |
| Ethanol (ethyl alcohol) | balance ml |
| Urea Peroxide | .001-40 g |
| Resin | .001-30 g |
| Hydroxyl propyl cellulose | .001-20 g |
| total | 100 ml |

A further embodiment of the whitening agent follows.

| WHITENING AGENT COMPOSITION A4 (total yield 100 ml of composition) | |
| --- | --- |
| Ethanol (ethyl alcohol) | balance ml |
| Urea Peroxide | 8 g |
| Resin | 10 g |
| Hydroxyl propyl cellulose | .5 g |
| total | 100 ml |

Whitening agent of composition A3 may be made with 100% pure undenatured ethyl alcohol and 98% pure urea peroxide.

Rosin may be substituted for resin in all formulas.

Urea hydrogen peroxide may be substituted for urea peroxide in all formulas.

Whitening agents may be formulated as follows:

| WHITENING AGENT COMPOSITION A5 (total yield 100 ml of composition) | |
| --- | --- |
| Rosin | .001-30 g |
| Urea hydrogen peroxide | .001-40 g |
| Hydroxypropyl cellulose 1500 cps | .001-20 g |
| Ethyl alcohol (95%) | balance ml |
| Total Volume | 100 ml |

The following is an example of a tooth whitening compound that has been formulated in accordance with the invention.

The following is the formulation of a procedure for making 100 ml of a Solution No. 16.

In the following formula, the resin, the urea hydrogen peroxide USP, and the hydroxypropyl cellulose 1500 cps are all expressed as a weight per volume (w/v; i.e., g/100 ml) and the ethanol 95 was added in a quantity as needed (q.s.) to yield the desired 100 ml of whitening agent.

| WHITENING AGENT COMPOSITION OF SOLUTION NO. 16 (total yield 100 ml of composition) | |
| --- | --- |
| Rosin | 12.5 g |
| Urea hydrogen peroxide | 8.0 g |
| Hydroxypropyl cellulose 1500 cps | 0.5 g |
| Ethyl alcohol (95%) | balance mll |
| Total Volume | 100 ml |

Solution No. 16 was formulated as follows to yield 100 ml of product:
1. Dissolve 12.5 g of resin in 75 ml of the ethanol in a beaker having a spin bar therein;
2. The spin bar was spun using the spinning device (stirrer) of an unheated hot plate of the type having a magnetic stirrer disposed therein, the spinning was continued until the unheated rosin and ethanol solution was clear;
3. 8 g of the urea hydrogen peroxide were weighed out and ground into a fine powder using a mortar and pestle, added to the rosin and ethanol solution, and then stirred on the spinning device. A cloudy solution resulted.
4. As the rosin and ethanol solution was spinning, the 0.5 g of hydroxypropyl cellulose was added gradually (sprinkled into the vortex of the spinning solution resulting from the magnetic stir bar) in small amounts at a time. The spinning was continued for about an hour until the solution began to gel. Enough ethyl alcohol (95%) was added q.s. to bring the volume up to 100 ml, and the spinning was continued.
5. The mixed solution was put in a refrigerator (at about 40° F.) and left overnight (i.e., about 19-20 hours) to allow the solution to completely hydrolyze.
6. The refrigerated solution was removed from the refrigerator and again spun at room temperature at about 70° F.) for about 30 minutes to thoroughly mix the solution.

The prepared solution was then put into the desired containers.

It should be noted that in Step 4 of spinning the solution having the rosin, the urea hydrogen peroxide 1500 cps, and the hydroxypropyl cellulose, the added materials may not thoroughly dissolve. It appears that the step of allowing the solution to sit overnight in the refrigerator for a period of time, and then remixing the solution succeeds in yielding a homogeneous solution with the added materials dissolved and dispersed throughout.

The following is the formulation of a Solution No. 18 that has been made.

| WHITENING AGENT COMPOSITION OF SOLUTION NO. 18 (total yield 60 ml (i.e., 51.43 g) of composition) | |
| --- | --- |
| Rosin | 7.5 g |
| Urea hydrogen peroxide | 3.6 g |
| Hydroxypropyl cellulose 1500 cps | 0.3 g |
| Ethyl alcohol (95%) | 40.0 g |
| Spearmint Extract (1 drop) | 0.03 g |
| Total Weight | 51.43 g |

Thus, Solution No. 18 can be expressed on a weight per weight (w/w) basis of about 14.6% rosin; 7.0% urea hydrogen peroxide; 0.6% hydroxypropyl cellulose 1500 cps; 77.8% ethyl alcohol; and 0.06% spearmint extract; the total is not exactly 100% owing to the rounding of the percentages to one (1) significant digit.

Solution No. 18 was prepared in a manner analogous to that as described above in connection with the preparation of Solution No. 16.

Detailed Description of the Hand Held Consumer Light

The present invention provides a light source for tooth whitening which uses a battery or a rechargeable power supply and, which may be held by the consumer (i.e., the patient) outside the patient's mouth in a manner to provide a uniform illumination of the patient's anterior teeth to produce a uniform increase in temperature of the anterior surfaces of the anterior teeth from about 1° C. to a maximum of 5° C. over a period of application of a maximum of 10 minutes. Also the light emits a biologically safe wavelength of visible light between 350-700 nanometers, which can penetrate the tooth and react with the photoactivator substance speeding the release of the oxidizing compound.

As described in the literature, an unexpected benefit of utilizing a transparent solution or gel containing the oxidizing compound is that certain visible wavelengths of light seem to be absorbed by tooth chromogens (stains) in a manner that promotes their oxidation to a non-chromogenic state. Reflectance studies demonstrate that enamel and dentin transmit green light, reflect yellow and red light, and absorb blue light. Light can be absorbed by the molecules responsible for tooth discoloration, thus the chromogens may, in effect, act as photosensitizers. In theory, light of a visible wavelength may utilize a tooth chromogen molecule as a photosensitizer in order to improve the efficiency of the oxidizing agent to remove the chromogen (stain). Yet, prior to the present invention no one had previously reduced light intensity levels-to levels which could be used by a consumer with effective tooth whitening results.

The device illustrated in FIGS. 1-6 is a consumer hand-held light source according to the invention that is capable of generating a desired amount of heat of approximately 1°-5° C. within 2 mm of the tooth surface. This may be considered a desired temperature increase. The desired temperature increase may be administered up to about 10 minutes. An example of a known light source that meets these requirements is a Xenon light. Other light sources may be Quartz or Halogen light sources or other sources not limited to the ones described, as will be readily apparent to a person having ordinary skill in the art.

Figure 1:
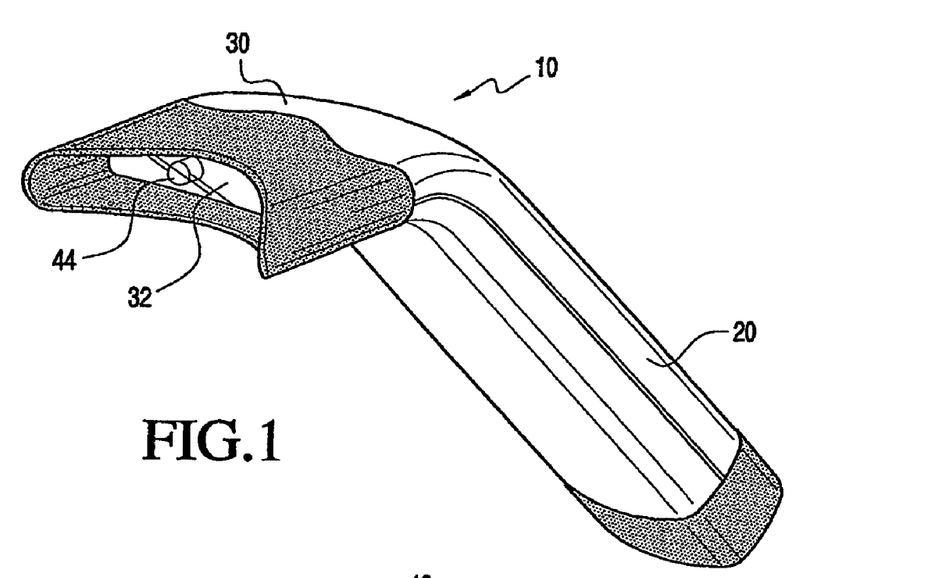
FIG. 1 shows a left side view of an embodiment of a hand-held consumer light for use with a tooth whitening system according to the invention.
Figure 2:
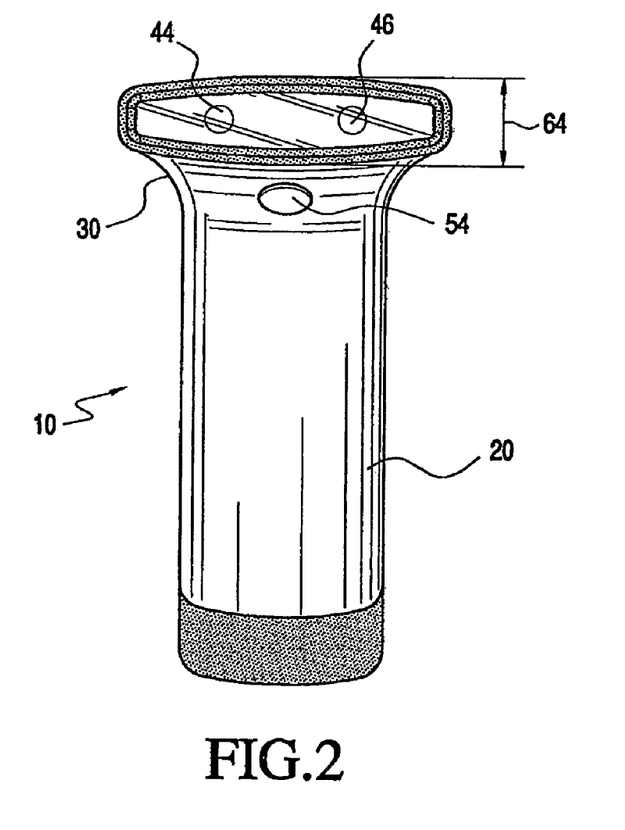
FIG. 2 shows a front view of the hand-held consumer light of FIG. 1 for use with the tooth whitening system according to the invention.
Figure 3:
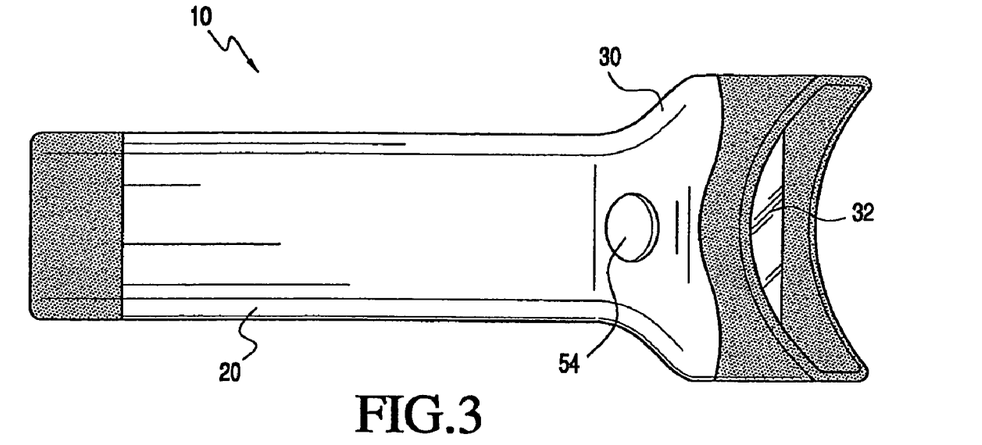
FIG. 3 shows a bottom view of the hand-held consumer light of FIG. 1 for use with the tooth whitening system according to the invention.
Figure 4:
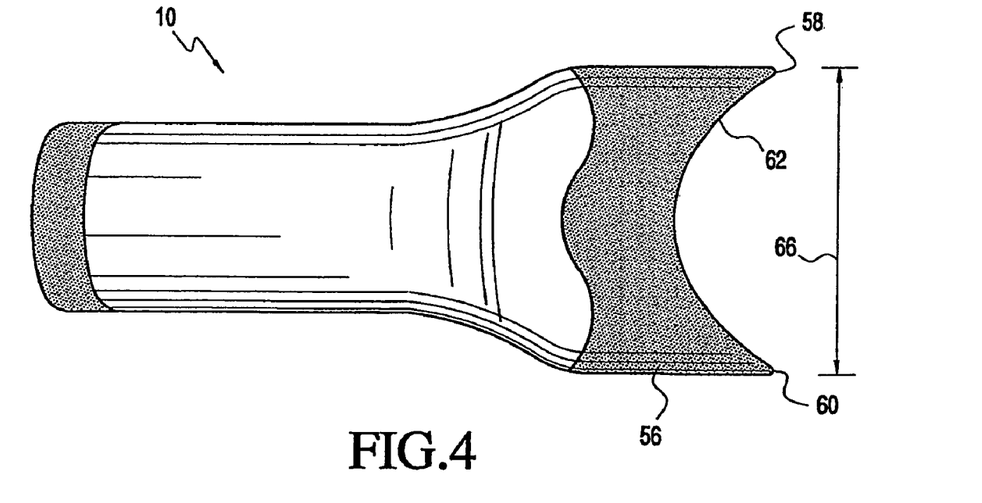
FIG. 4 shows a top view of the hand-held consumer light of FIG. 1 for use with the tooth whitening system according to the invention.
Figure 5:
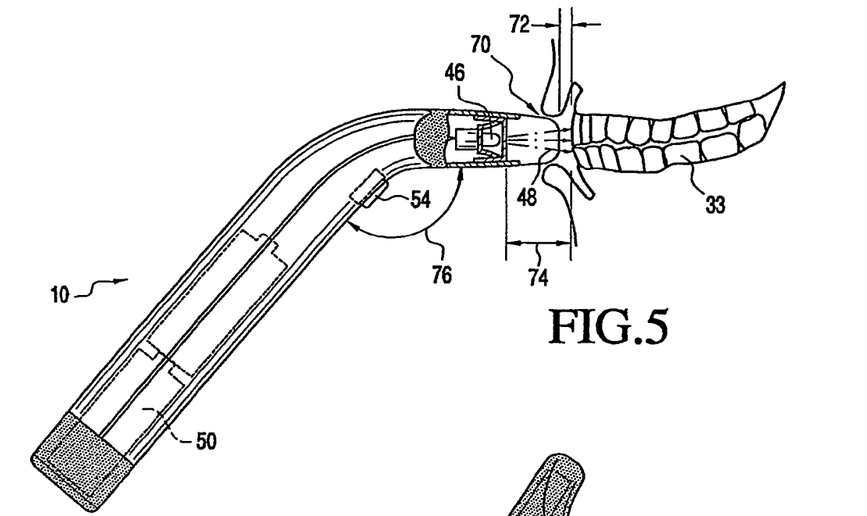
FIG. 5 shows a right, partially broken away side view of the hand-held consumer light of FIG. 1 in use.
Figure 6:
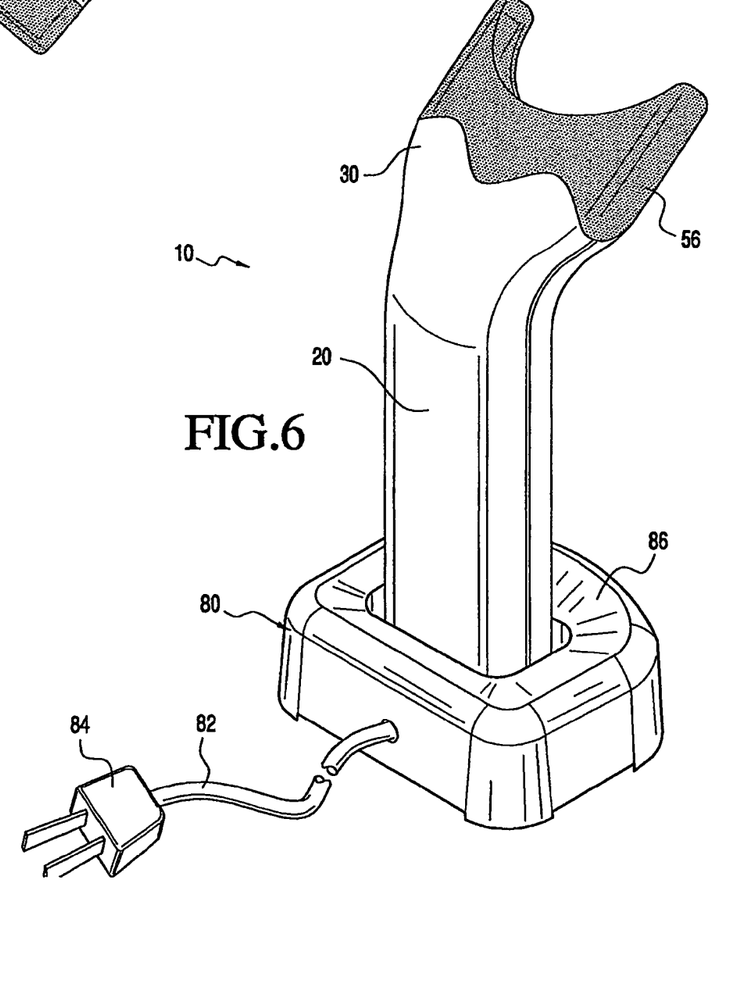
FIG. 6 shows a perspective view of the hand-held consumer light for use with the tooth whitening system according to the invention in an optional recharger base.

The power source shown in the FIGS. 1-6 is battery power for convenience; however, direct current may also be considered enabling the device to be free-standing. FIG. 6 shows the power source may include a rechargeable battery.

Attachment(s) which may be used with above-described inventive hand-held consumer light containing the illuminating bulb(s) will be shaped to follow the natural curvature of the upper arch enabling an even disbursement of light and heat to all the anterior teeth to provide even whitening results. Attachments may be provided in various sizes to facilitate different size arches—large, medium and small.

Another attribute of the attachment is that it may be enclosed, completely or partially, by an encompassing soft material which will act as a cheek and lip retractor keeping the light source a given required distance from the tooth surface to produce the temperature range required and to isolate the teeth while the light is activated. The light sources capable of causing a desired increase in temperature are considered to be included in this invention. The desired temperature increase may be as described above. Infrared light more readily penetrates the tooth structure and may cause an excessive temperature rise in the pulp. Suitable bulbs which can produce heat are linear flash lamps, tungsten, halogen, metal halides, xenon short arc and, mercury short arc, as well as others which achieve the desired results.

FIGS. 1-6 illustrate an embodiment of a hand-held light source 10 for use with a tooth whitening system according to the invention.

Light source 10 may include a handle 20 and an upper part or head 30. A blue lens 32 having a perimeter may be provided. Blue lens 32 filters out certain wavelengths of light, which wavelengths may be undesirable wavelengths of light, depending on the methodology consistent with the invention. Lens 32 allows the desired wavelengths of light to pass through. Lens 32 may be provided on head 30 and be configured in the desired shape to assist in causing light rays to be directed at and strike the whitening compound applied to a user's teeth 33 in the desired amount and intensity for causing the predetermined chemical reaction effecting the whitening of the teeth, along the lines described above. A blue light filter which filters out undesirable wavelengths of light may be provided, the blue light filter thus enabling a blue wavelength to be emitted to penetrate the tooth.

In order to provide the desired light and/or heat source, one or more light sources or elements or bulbs may be provided, such as the illustrated light bulbs 44 and 46.

Light rays 48 of the desired wavelength and intensity are schematically shown in FIG. 5.

A power source 50, such as a battery, alternating or direct current, as desired, may likewise be provided. Also, rechargeable batteries may be utilized.

It will be appreciated that the configuration and the location of light sources 44 and 46, as shown in the illustrated array, will effect the desired consistent, uniform chemical reaction of the tooth whitening agent provided on the user's teeth, in use.

Light source 10 may further be provided with an on-off switch 54 for controlling the administering of light from the light source. A timer may be provided for controlling the length of time the light source may be used within a given period of time, regardless of the number of times the user actuates switch 54. Alternatively, light bulbs 44 and 46 may be activated (i.e. ON) only when switch 54 is actuated.

One or more attachments 56 may be provided to accommodate different sizes, widths, and arch sizes of the user's mouth. Attachment 56 may be provided with one or more extensions 58 and 60, as well as with a predetermined curvature 62, dependent on the size requirements of the user's mouth, as outlined above. In addition, a height 64 and a width 66, as well as other configuration considerations will be taken into account, dependent on the user's mouth contour, and the type of light source 44 and 46 provided, for example.

In use, thanks to the configuration of attachment 56 and its associated configured extensions, size, and shapes, attachment 56 will contact the lips and mouth tissue in a region 70, as shown in FIG. 5. This contact region 70 establishes a predetermined distance 72 between attachment 56 and teeth 33. Thus, a desired offset or spacing 74 between lens 32 and light sources 44 and 46 and teeth 33 is established. In that manner, the intensity of light rays 48 is governed and predetermined so that the predetermined degree of temperature increase within the outer 2 mm of the tooth surface is established, as described above.

Still further, thanks to the establishment of a predetermined angle 76 between head 30 and handle 20 of the housing of light source 10, the user is able to comfortably and accurately direct light rays 48 at teeth 33 in the desired manner. Handle 20 of the housing is configured for being manipulated by a user. Lens 32 is provided on head 30 of the housing at a distance from handle 20. And head 30 of the housing is disposed relative to handle 20 at a predetermined angle so that, in use, a user may direct light emitted by the light element 44, 46 and direct heat transmitted by the light element 44, 46, at the user's own teeth 33, as shown in the Figs. Handle 20 extends at an angle of about 45°-135° relative to a direction of extension of the head 30 of the housing. In other words, head 30 extends at an angle of about 45°-135° relative to a direction of extension of handle 20. Thus, the goal of home use by a person whose teeth 33 are to be whitened is achieved.

FIG. 6 illustrates a recharger 80 which may be provided for recharging rechargeable battery 50.

Recharger 80 may be provided with an electrical cord 82 and a plug 84, as will be readily understood by a person having ordinary skill in the art. In the case where the recharger is powered by alternating current, such as typical AC household electrical outlets, an AC to DC convert/transformer or a microchip to convert AC effectively into DC may be provided in the recharger base 86, as will be readily understood. Base 86 may be configured for being freestanding and sized and weighted so that light source 10 may be placed on a countertop for recharging, as shown.

In use, it will have been appreciated that the user may bare his or her teeth 33, such as by smiling, and face lens 32 at the same level and orientation as lens 32 of FIG. 5, with light source 10 disposed substantially adjacent the teeth, as shown, and as described above.

There may be a fiber optic strand or cable or device to guide and direct light from the light source to a desired location.

The location may be selected so as to illuminate and whiten one or more of the user's teeth.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention or limits of the claims appended hereto.

What is claimed is:

1. A tooth whitening system, comprising:
 a) a portable, self-contained, hand-held light source;
 b) the hand-held light source including:
  i) a housing;
  ii) the housing including a handle configured for being manipulated by a user;
  iii) a head;
  iv) a blue lens having a perimeter and provided on the head of the housing at a distance from the handle, the blue lens filters out undesirable wavelengths of light, the blue lens causing a blue wavelength to be emitted to penetrate a user's tooth;
  v) a self-contained xenon light provided in the housing and located for emitting light through the blue lens, the xenon light, in use, emitting light of a wavelength suitable for activating a light-activated tooth whitener, and the xenon light transmitting heat sufficient for heating a user's tooth, in use, when a tooth whitener is provided on a user's teeth;
  vi) a power source provided in the housing, the power source being electrically connected with the xenon light;
  vii) a switch being provided, the switch being electrically connected with the power source for switching the xenon light on and off when actuated;
  viii) a timer being provided for controlling the length of time the xenon light may be used within a given period of time, regardless of the number of times a user actuates the switch;
  ix) the head of the housing being disposed relative to the handle at a predetermined angle of about 45°-135° relative to a direction of extension of the handle of the housing, so that, in use, a user may direct light emitted by the xenon light, and direct heat transmitted by the xenon light, at the user's own teeth;
  x) an attachment being provided on the head of the housing and being configured to accommodate a width and arch size of the user's mouth; and
  xi) the attachment extending around the perimeter of the blue lens and including a predetermined curvature, a height, and a width to contact the lips and mouth tissue of the user in a contact region to establish a predetermined distance between the attachment and the user's teeth, and to establish a desired offset between the blue lens and the xenon light and the user's teeth to govern and predetermine the temperature increase within the outer 2 mm of the tooth surface of the user's teeth and to produce a uniform increase in the temperature of the outer 2 mm of the user's anterior teeth from about 1° C. to a maximum of 5° C. within 2 mm of the tooth surface.

2. A tooth whitening system as in claim 1, wherein:
 a) the xenon light includes two xenon light bulbs.

3. A tooth whitening system as in claim 1, wherein:
 a) the xenon light includes a xenon short arc light bulb.

4. A tooth whitening method, comprising:
 a) providing a portable, self-contained, hand-held light source including:
 b) the hand-held light source including:
  i) a housing;
  ii) the housing including a handle configured for being manipulated by a user;
  iii) a head;
  iv) a blue lens having a perimeter and provided on the head of the housing at a distance from the handle, the blue lens filters out undesirable wavelengths of light, the blue lens causing a blue wavelength to be emitted to penetrate a user's tooth;
  v) a self-contained xenon light provided in the housing and located for emitting light through the blue lens, the xenon light, in use, emitting light of a wavelength suitable for activating a light-activated tooth whitener, and the xenon light transmitting heat sufficient for heating a user's tooth, in use, when a tooth whitener is provided on a user's teeth;
  vi) a power source provided in the housing, the power source being electrically connected with the xenon light;
  vii) a switch being provided, the switch being electrically connected with the power source for switching the xenon light on and off when actuated;
  viii) a timer being provided for controlling the length of time the xenon light may be used within a given period of time, regardless of the number of times a user actuates the switch;
  ix) the head of the housing being disposed relative to the handle at a predetermined angle of about 45°-135° relative to a direction of extension of the handle of the housing, so that, in use, a user may direct light emitted by the xenon light, and direct heat transmitted by the xenon light, at the user's own teeth;
  x) an attachment being provided on the head of the housing and being configured to accommodate a width and arch size of the user's mouth; and
  xi) the attachment extending around the perimeter of the blue lens and including a predetermined curvature, a height, and a width to contact the lips and mouth tissue of the user in a contact region to establish a predetermined distance between the attachment and the user's teeth, and to establish a desired offset between the blue lens and the xenon light and the user's teeth to govern and predetermine the temperature increase within the outer 2 mm of the tooth surface of the user's teeth and to produce a uniform increase in the temperature of the outer 2 mm of the user's anterior teeth from about 1° C. to a maximum of 5° C. within 2 mm of the tooth surface; and
b) providing a tooth whitener on a user's teeth.

5. A tooth whitening method as in claim 4, wherein:
a) a mouth rinse is provided, the mouth rinse being selected for preconditioning a user's teeth for receiving a whitening compound.

6. A tooth whitening method as in claim 5, wherein:
a) the mouth rinse includes a mouth rinse having a formula:

| Ingredient | Concentration |
|---|---|
| NP-9, ethoxylated nonylphenol, 9 molar EO. | 0.65 mls |
| Peppermint Oil | 1.4 mls |
| Nutrasweet ® Granular 100 | 0.75 grams |
| Glycerin 99.5% Kosher food grade | 30 mls |
| Sodium Bicarbonate food grade | 2 grams |
| Sodium Carbonate food grade | 0.1 grams |
| Benzethonium Chloride | 0.15 grams |
| Purified Water | Balance to 1 gallon (i.e., 3.785 liter) |
| Ethanol 75% or greater | ~10 mls. |

7. A tooth whitening method as in claim 4, wherein:
a) the tooth whitener includes a light-activated tooth whitener provided on a user's teeth.

8. A tooth whitening method as in claim 4, wherein:
a) the tooth whitener includes a heat-activated tooth whitener provided on a user's teeth.

9. A tooth whitening method as in claim 4, wherein:
a) a preconditioning rinse is provided, the preconditioning rinse being formulated to pretreat the environment of the user's teeth to be in a pH range of about 7.9-9.0.

10. A tooth whitening method as in claim 9, wherein:
a) the preconditioning rinse is formulated to kill bacteria which produce peroxidase enzymes.

11. A tooth whitening method as in claim 4, wherein:
a) the tooth whitener includes a tooth whitener having a formula:

| COMPOUND | % by Weight | RANGE % |
|---|---|---|
| Ethyl Alcohol | 73.75 | |
| Hydrogenated Ester of Rosin | 13.87 | 0.001-35.00 |
| Urea (Carbamide) Hydrogen Peroxide | 11.10 | 0.001-25.00 |
| Hydroxypropylcellulose 1500 cps | 0.55 | 0.001-10.00 |
| Flavoring - Menthol | 0.22 | 0.001-15.00 |
| Flavoring - Peppermint Oil | 0.20 | 0.001-15.00 |
| Zinc Oxide (micro particles) | 0.15 | 0.001-5.00 |
| Flavoring - Aspartame | 0.15 | 0.001-5.00. |

* * * * *